United States Patent [19]
Eck et al.

[11] Patent Number: 5,755,975
[45] Date of Patent: May 26, 1998

[54] SEPARATION OF SUBSTANCES FROM A LIQUID MIXTURE BY CRYSTALLIZATION

[75] Inventors: Bernd Eck, Viernheim; Bernhard Maltry, Obrigheim, both of Germany

[73] Assignee: BASF Aktiengesellschaft, Ludwigshafen, Germany

[21] Appl. No.: 708,821

[22] Filed: Sep. 9, 1996

[30] Foreign Application Priority Data

Oct. 2, 1995 [DE] Germany .................. 195 36 792.8

[51] Int. Cl.$^6$ ...................................... C02F 1/22
[52] U.S. Cl. .................. 210/714; 62/532; 62/541; 23/295 R; 23/296; 23/301
[58] Field of Search .................. 62/532, 541; 23/295 R, 23/296, 301, 300; 210/714

[56] References Cited

U.S. PATENT DOCUMENTS

| | | | |
|---|---|---|---|
| Re. 32,241 | 9/1986 | Saxer | 62/542 |
| 3,621,664 | 11/1971 | Saxer | 62/58 |
| 3,844,724 | 10/1974 | Sloan . | |
| 4,004,886 | 1/1977 | Thijssen et al. | 62/544 |
| 4,493,719 | 1/1985 | Wintermantel et al. | 62/532 |
| 4,552,575 | 11/1985 | Stolzenberg et al. | 62/544 |
| 4,657,559 | 4/1987 | Mollere et al. | 23/301 |
| 4,776,177 | 10/1988 | Jancic et al. | 62/123 |
| 4,787,985 | 11/1988 | Roodenrijs et al. | 23/301 |
| 4,795,571 | 1/1989 | Holzknecht | 210/774 |
| 5,329,021 | 7/1994 | Cohen et al. | 548/543 |
| 5,434,316 | 7/1995 | Kissinger | 568/724 |

FOREIGN PATENT DOCUMENTS 37 08 709  3/1987  Germany .

Primary Examiner—Neil McCarthy
Attorney, Agent, or Firm—Keil & Weinkauf

[57] ABSTRACT

In a process for separating substances from a liquid mixture by crystallization in a crystallizer, a two-phase seed layer in the form of a melt or solution of the mixture to be separated, with crystals suspended therein, is applied, prior to the crystallization, to those surfaces of the crystallizer from which crystals grow during the crystallization.

9 Claims, No Drawings

SEPARATION OF SUBSTANCES FROM A LIQUID MIXTURE BY CRYSTALLIZATION

The present invention relates to a process for separating substances from a liquid mixture by crystallization.

Crystallization, in particular fractional crystallization, is a thermal separation process which is preferably used for the separation of liquid mixtures Crystallization is particularly effective for separating heat-sensitive substances, azeotropic mixtures or substances having low relative volatilities.

The processes of fractional crystallization are based on the formation or the growth of crystals on cooled surfaces. The mixture to be purified is introduced into the appropriate crystallizer, and a solid phase which differs in its composition from the liquid phase is then frozen out on the cooled surfaces. After a certain proportion of the mixture used has been frozen out, the liquid residual phase is separated off. This is usually effected by simply allowing the residual phase to run off. German Laid-Open Application DOS 2,606,364 describes a process for separating substances from a liquid mixture by fractional crystallization, in which the liquid mixture is repeatedly passed into turbulent flow through an indirectly cooled crystallization zone, with the proviso that the crystallization zone is always full. A further development of this process is described in EP-B 0 279 439 and German Laid-Open Application DOS 3,708,709, in which the crystal layers frozen out on a cooled surface are brought into contact with a purification solution and thus purified. The two last-mentioned applications also disclose the presence of a thin seed crystal layer on the cooled surfaces, which is formed by a crystallized trickle film from the preceding crystallization stage after removal of the melt. For the formation of this seed crystal layer, strong supercooling is necessary after discharge of the crystals in the preceding crystallization stage.

German Published Application DAS 1,769,123 states that the crystallization must be initiated by the formation of local centers of crystallization as a result of strong supercooling. The initiation of crystallization by spontaneous nucleation due to strong supercooling of a thin liquid film which originates from the preceding crystallization is stated as a further variant. It is also pointed out that the spontaneous nucleation must take place at particularly low coolant temperatures. The particular disadvantage here is that a large amount of energy is required for the cooling.

The disadvantage for supercooling is that the entire crystallizer has to be cooled. After the seed layer has frozen solid, the entire apparatus must be heated up again to a temperature close to the equilibrium temperature since uncontrolled crystal growth would occur at the beginning of crystallization owing to the excessively large temperature differences between seed layer and equilibrium layer of the melt to be purified. Heating up the apparatus prior to the crystallization has considerable disadvantages with regard to energy, depending on the preceding supercooling.

EP-B 0 218 545 points out that the beginning of crystallization may present problems in the case of certain materials, ie. the initiation of crystal formation is often not reproducible. To solve this problem, the patent proposes providing baffles in the crystallization apparatus, which are advantageously perforated in order to improve the liquid distribution at the beginning of the crystallization. The disadvantage here is the energy required for cooling and heating the baffles, apart from the additional cost with respect to the apparatus.

It is an object of the present invention to modify the processes for separating substances by fractional crystallization in such a way that, compared with the processes known to date, substantial advantages are achieved with regard to the complexity of the purification procedure and hence the cost-efficiency of the purification.

We have found, surprisingly, that this object is achieved if a two-phase seed layer consisting of melt or solution and crystals of the mixture to be separated which are suspended in this melt or solution is applied, prior to the crystallization, to those surfaces of the crystallizer from which crystals grow during the crystallization.

The present invention therefore relates to a process for separating substances from a liquid mixture by crystallization in a crystallizer, wherein a two-phase seed layer in the form of a suspension of a melt or solution of the mixture to be separated, with crystals of the mixture suspended therein, is applied, prior to the crystallization, to those surfaces of the crystallizer from which crystals grow during the crystallization. Preferred embodiments of the process are defined in the subclaims.

According to the invention, the term seed layers here also includes crystals settled out from a suspension and frozen solid on a crystallizer surface.

The invention has the advantage that supercooling of the melt or solution is no longer required for initiating the crystallization of the seed layer. Uncontrolled crystal growth, which easily leads to inclusions of impurities and hence reduces the purification effect, is thus avoided. Moreover, initiation of the crystallization is reproducible in every case. In addition, it was found that a melt or solution containing suspended crystals wets the surfaces of the crystallizer better than a single-phase seed layer as described in EP-B 0 218 545, German Published Application DAS 17 69 123 and German Laid-Open Application DOS 37 08 709. The better wetting leads to homogeneous covering of the crystallizer with a seed layer and hence also to a considerably improved separation effect in the crystallization. The purification effect of the crystallization is thus improved without the need for any additional baffles, as envisaged in EP-B 0 218 545, or super-cooling of the melt and of the crystallizer, as described in German Published Application DAS 1,769,123, which leads to the abovementioned disadvantages.

The procedure for the novel crystallization process is not subject per se to any restrictions. In principle, all crystallizers whose mode of operation is based on the formation of crystals on cooled surfaces may be used. The novel process can be carried out as a dynamic or static process or as a combination of these two processes. In the static process, as described, for example, in U.S. Pat. 3,597,164, European Patent 0 323 377 and French Patent 2,668,946, the liquid phase is moved only by free convection, whereas in the dynamic process the crystallization is carried out with forced convection of the liquid phase. This can be effected by forced flow in completely flow-through heat transfer apparatuses, as described, for example, in German Patent 26 06 364, or by applying a trickle film to a cooled wall, as described, for example, in German Published Application DAS 17 69 123 and EP-B 0 218 545.

The novel process can be used both for crystallization from the melt of the substance to be separated off and for crystallization from a solution of the substance to be separated off in a solvent and is generally suitable for all substances which can be crystallized on a cooled surface. Fractional crystallization from the melt is of particular industrial importance. Liquid mixtures particularly suitable for the separation are those which have a melting point of from −50° to +300° C., do not decompose at the temperatures used and preferably contain, for example, N-vinylpyrrolidone, naphthalene, anthracene, bisphenol A, benzoic acid, monochloroacetic acid, acrylic acid, methacrylic acid, piperazine, caprolactam, xylene (isomer separation), hexamethylenediamine, toluene diisocyanates (isomer separation) and diphenylmethane diisocyanate (methylenedi(phenyl isocyanate); isomer separation).

The suspension used in the novel process can be produced in different apparatuses. In a preferred embodiment of the invention, crystals are frozen out from a melt or solution of the mixture to be separated and are introduced into the melt or solution. Preferably, crystals are frozen out by indirect cooling in scraped-wall coolers or stirred kettles, in particular having stirrers passing close to the wall, and are transported with the aid of scraping elements from the cooled walls into the suspension. It is also possible to produce crystals directly in the melt or solution by cooling the melt or solution, either by means of the crystallizer itself or by means of coolable elements (for example, cold fingers, cooling zones or stirred containers) installed in the crystallizer or other apparatuses, and to produce a suspension in this manner. This has the advantage that the crystals need not be scraped off. The use of coolable elements is advantageous since it is not necessary to cool the entire crystallizer. It is also possible to produce a suspension in the crystallizer or outside it and to allow the crystals to settle out of the suspension in the crystallizer onto the crystallization surface, where they act as seed crystals. The solids content of the suspension is from 0 to 60 g of solid/g of suspension.

In a preferred embodiment of the invention, the suspension is applied to the crystallizer surfaces by filling the crystallizer with the suspension and then emptying it. After emptying, a suspension layer remains on the crystallizer surfaces and is then frozen (at its equilibrium temperature). A corresponding procedure can be adopted when the suspension is produced in the crystallizer itself. It is also possible to apply the suspension to the crystallizer surfaces by means of conventional distributor apparatuses, such as overflow weirs, nozzles or slotted distributors. This makes it possible to avoid filling of the apparatus with subsequent emptying.

Processes for carrying out the crystallization which are suitable according to the invention are described, for example, in U.S. Pat. No. 5,329,021, German Patents 26 06 364 and 17 69 123 and European Patent 0 475 893. According to the invention, the mixture to be purified is introduced as a melt or solution into the crystallizer after application of the seed layer, and a solid crystal phase is then frozen out on the cooled surfaces of the crystallizer. Since a crystalline phase is present as a seed layer as early as the beginning of the crystallization steps, the mixture to be purified need no longer be supercooled for formation of crystals. During filling of the crystallizer, the melt or solution to be purified is either at the melting point or a few degrees Celsius above the melting point, in order to avoid the formation of crystals in the feed pipes. When the crystals have settled out from the suspension and frozen solid, there is no longer any need for emptying and subsequent filling with crude melt or crude solution. In this case, crystallization can be carried out immediately.

After a certain proportion of the mixture used has been frozen out, the two phases are separated from one another, which may be effected, for example, by simply draining away or pumping away the liquid residual phase. The crystalline phase separated off is then heated to a temperature at which the crystals liquefy, and this melt or solution is, if necessary, subjected to further crystallization steps. The residual phase may also be subjected to further crystallization steps, as described in detail further below. The crystallization may be followed by further purification steps. Washing of the crystalline layer with purification liquid, as described, for example, in German Laid-Open Application DOS 37 08 709, and/or sweating of the crystalline layer are particularly suitable. During sweating, the temperature of the crystalline layer is increased, the more highly contaminated parts of the crystalline layer melting away and an additional purification effect thus being achieved.

The novel process is carried out in one or more crystallization stages. In general, the crystallization stages may be divided into purification stages and expulsion stages. In order to increase the separation effect, a crystallization stage may be followed by further purification (crystallization) stages, in each of which the crystals of the preceding stage are crystallized. In order to increase the yield of the process, it is possible to provide expulsion stages in which the liquid residual phase is subjected to expulsion (crystallization) stages. The procedure here is preferably based on the countercurrent principle, in which the streams of crystals are fed to the stages with the next highest stage number and the streams of crystallization residue are fed to the stages with the next lowest stage number. The number of crystallization stages and hence also of purification and expulsion stages depends on the separation task and may be determined by conventional experiments by a person skilled in the art.

In principle, any composition of the melt or solution which occurs in the process may be used for producing the suspension. In a preferred embodiment of the invention, a melt or solution which is purer than the melt or solution to be crystallized in the particular stage is used for producing the suspension. The molten crystals leaving the particular crystallization stage are preferably used.

The invention is illustrated by the following Example, which is a preferred embodiment of the invention.

EXAMPLE

N-Vinylpyrrolidone having an initial impurity content of 0.6% by weight (based on 100% by weight of N-vinylpyrrolidone (this concentration of impurities corresponds to the concentration of impurities which is stated in U.S. Pat. No. 5,329,021)) was crystallized in a crystallizer as described in DE-A 26 06 364 (BASF), in two purification stages and four expulsion stages. A two-phase suspension consisting of N-vinylpyrrolidone melt containing suspended N-vinylpyrrolidone crystals was applied as a seed layer to the surfaces of the crystallizer in all crystallization stages. In order to produce the seed layer, the crystallizer was filled with the melt to be purified in the particular stage and a suspension was produced by cooling the apparatus. The apparatus was then emptied and the suspension remaining on the crystallizer surfaces was frozen solid. The equilibrium temperatures of the melts during the crystallization in the individual stages were as follows:

| Purification stage 5: | 13.5 to 12.9° C. |
|---|---|
| Purification stage 6: | 13.8 to 13.6° C. |
| Expulsion stage 1: | 13.1 to 12.6° C. |
| Expulsion stage 2: | 12.5 to 11.4° C. |
| Expulsion stage 3: | 11.2 to 8.5° C. |
| Expulsion stage 4: | 8.5 to 4.3° C. |

Except for expulsion stage 4, which was operated by a static procedure, all other stages were operated by a dynamic procedure. The ratio of the mass of crystals frozen out in one stage to the mass of crystals used in this stage was 0.8 in the first purification stage and 0.75 in the second purification stage. In the first purification stage, a concentration of impurities of 0.102% by weight (based on 100% by weight of N-vinylpyrrolidone) was achieved in the crystals. Compared with the U.S. Patent, this corresponds to a concentration of impurities which is lower by a factor of 4 (there, the concentration of impurities was 0.4% by weight, based on 100% by weight of N-vinylpyrrolidone). The crystals are then fed to a second purification stage and leave this stage with a concentration of impurities of 190 ppm, which is lower by a factor of about 2.5 compared with the U.S. Patent, in which the concentration of impurities was 500 ppm.

In comparison with known processes, a concentration of impurities in the purified N-vinylpyrrolidone which is lower by a factor of 2.5 is thus achieved by the novel process by applying a seed layer of N-vinylpyrrolidone prior to the particular crystallization, with the same starting conditions, the same number of purification stages and the same frozen-out mass of crystals, based on the melt or solution used. With the same product specification, this means fewer purification stages and hence a considerable reduction in the required cost of separation.

We claim:

1. A process for separating substances from a liquid mixture by crystallization in a crystallizer, wherein a two-phase seed layer in the form of a suspension of a melt or solution of the mixture to be separated, with crystals of the mixture suspended therein, is applied, prior to the crystallization, to those surfaces of the crystallizer from which crystals grow during the crystallization.

2. A process as claimed in claim 1, wherein the suspension is produced by freezing crystals out of a melt or solution of the mixture to be separated and introducing these crystals into the melt or solution.

3. A process as claimed in claim 1, wherein the seed layer is applied by introducing the suspension into the crystallizer or producing the suspension in the crystallizer itself, then emptying the crystallizer and freezing the suspension layer remaining on the crystallizer surfaces.

4. A process as claimed in claim 1, wherein the seed layer is applied by applying the suspension to the crystallizer surfaces by means of distributor apparatuses.

5. A process as claimed in claim 1, wherein the crystallization is carried out in one or more crystallization stages.

6. A process as claimed in claim 5, wherein, when the crystallization is carried out in at least two stages, a melt or solution which is purer than the melt or solution to be crystallized in the particular stage is used for producing the suspension.

7. A process as claimed in claim 1, wherein the crystallization is carried out statically or dynamically.

8. A process as claimed in claim 1, wherein liquid mixtures having a melting point of from −50 to +300° C. are used.

9. A process as claimed in claim 1, wherein said liquid mixtures contain one or more compounds selected from the group consisting of N-vinylpyrrolidone, naphthalene, anthracene, bisphenol A, benzoic acid, monochloroacetic acid, acrylic acid, methacrylic acid, piperazine, caprolactam, xylene, toluene diisocyanate, diphenylmethane diisocyanate and hexamethylenediamine.

\* \* \* \* \*